(12) United States Patent
Guzman Pantoja et al.

(10) Patent No.: US 11,504,701 B2
(45) Date of Patent: Nov. 22, 2022

(54) CATALYTIC FORMULATION FOR PRODUCING PROPYLENE CYCLIC CARBONATE FROM CARBON DIOXIDE USING A POTASSIUM IODIDE CATALYST

(71) Applicant: INSTITUTO MEXICANO DEL PETROLEO, Mexico City (MX)

(72) Inventors: Javier Guzman Pantoja, Mexico City (MX); Edith Meneses Ruiz, Mexico City (MX); Candido Aguilar Barrera, Mexico City (MX); Andrea Rodriguez Hernandez, Mexico City (MX); Isidoro Garcia Cruz, Mexico City (MX); Jose Antonio Munoz Arroyo, Mexico City (MX); Juan Carlos Gaytan Ramos, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 72 days.

(21) Appl. No.: 17/100,938

(22) Filed: Nov. 22, 2020

(65) Prior Publication Data
US 2021/0162379 A1 Jun. 3, 2021

(30) Foreign Application Priority Data
Nov. 28, 2019 (MX) .................... MX/a/2019/014232

(51) Int. Cl.
| | | |
|---|---|---|
| *B01J 27/18* | (2006.01) | |
| *B01J 21/04* | (2006.01) | |
| *B01J 21/18* | (2006.01) | |
| *B01J 31/06* | (2006.01) | |
| *B01J 31/26* | (2006.01) | |
| *C07D 317/36* | (2006.01) | |
| *B01J 27/08* | (2006.01) | |

(52) U.S. Cl.
CPC ........... *B01J 27/1806* (2013.01); *B01J 21/04* (2013.01); *B01J 21/18* (2013.01); *B01J 27/08* (2013.01); *B01J 31/06* (2013.01); *B01J 31/26* (2013.01); *C07D 317/36* (2013.01); *B01J 2231/325* (2013.01); *B01J 2531/002* (2013.01)

(58) Field of Classification Search
None
See application file for complete search history.

(56) References Cited

FOREIGN PATENT DOCUMENTS

JP    2004026904 A  *  1/2004

OTHER PUBLICATIONS

Machine-generated English translation of Kasuya et al. (JP 2004026904 A) (Year: 2004).*

* cited by examiner

*Primary Examiner* — Yun Qian
(74) *Attorney, Agent, or Firm* — FisherBroyles, LLP; Jason P. Mueller (57) ABSTRACT

This invention is related to the synthesis of organic carbonates from carbon dioxide and epoxides. It is particularly focused on the production of propylene cyclic carbonate from propylene oxide. The proposed catalytic materials includes a support made of aluminum oxyhydroxide (Catapal B®), nitric acid, acetic acid and/or phosphoric acid. An important stage is the physical and chemical conditioning of the catalytic materials and to this end, experimental methodologies such as spheronization and thermal treatments were implemented prior the evaluation process.

3 Claims, 6 Drawing Sheets

CATALYTIC FORMULATION FOR PRODUCING PROPYLENE CYCLIC CARBONATE FROM CARBON DIOXIDE USING A POTASSIUM IODIDE CATALYST

RELATED APPLICATIONS

This application claims priority under 35 U.S.C. § 119 to Mexican Patent Application MX/a/2019/014232, filed on Nov. 28, 2019, the disclosure of which is incorporated by reference.

TECHNICAL FIELD OF THE INVENTION

This invention belongs to the field of catalytic materials for the transformation of carbon dioxide into higher added value products.

BACKGROUND OF THE INVENTION

The technologies involved in the industrial production of propylene carbonate are related to different catalytic materials based on: transition metals, rare earth elements, phosphines, silanes, metal oxides, etc. What follows is a summary of some patents that illustrate the aforementioned systems.

The application of the European patent EP 0477472A1 describes the synthesis of cyclic carbonates from different epoxides using catalysts of the type ethyl(triphenyl)phosphonium bromide. Such compounds are used in the production of urethane resins free of isocyanate; for this reason, the process has been considered as environmentally friendly.

In the patent document U.S. Pat. No. 3,748,345 the use of catalysts suitable for the reaction between carbon dioxide and epoxy compounds is proposed. Such catalysts employ unsaturated Ni (0)-phosphine complexes. In this procedure, ethylene oxide reacted in the presence of a benzene solution in Ni $(PPh_3)_2$ at 100° C. and 35 bar for 12 h. The results show selectivity values from 50 to 95%.

Other catalysts based on quaternary ammonium compounds, amines, guanidines and amidines are also reported. The following compounds are employed specifically: triethylammonium bromide, benzyl-trimethyl-ammonium carbonate, triphenylphosphine, piperazine, tetramethylguanidine and imidazoles.

The European patent EP 2146977B1 deals with the synthesis of cyclic carbonates, employing aluminum complex salts as catalyst. The invention also provides a method for the manufacturing of such salts whose general formula is shown in (1).

(1) General Formula of Catalyst Based on Aluminum Salts

The catalyst can feature one or more chiral centers or can have racemic mixtures or mixtures enriched with enantiomers or stereoisomers.

The application of the European patent EP 2151465A1 describes the synthesis of polycarbonates prepared from biomass-derived cyclic monomers in the presence of a catalyst and a transfer agent. The formed polycarbonates are obtained from continuous polymerization with the addition of small amounts of catalytic metals to the transfer agents in order to produce glycerol-derived cyclic carbonates. Within the aluminum-based catalytic compounds, the following anions can be mentioned: triflate, triflimidate, acetylacetonate or carboxylate.

The European patent EP 2903974B1 develops a method for synthesizing cyclic carbonates using single-stage processes. Such compounds are obtained from aldehydes and $CO_2$, specifically from the Corey-Chaykovsky reaction, which consists of the following stages:

1.—To the aldehyde with general formula shown in the structure (2), NaOH is added under nitrogen atmosphere within a temperature interval ranging from 0 to 35° C. until obtaining a sludge-like substance.

R = alkyl, aryl, vinyl (2) General Formula of the Employed Aldehyde

2.—The Corey-Chaykovsky reagent $[(CH_3)_3SI$ or $(CH_3)_3SOI)]$ is added until producing a homogeneous solution.

3.—An aldehyde is added along with $CO_2$ bubbling until obtaining a homogeneous mixture within a temperature interval ranging from 40 to 60° C. during a period of time from 6 to 8 h.

In the application of the European patent EP 2990112A1 a method for manufacturing catalysts for the synthesis of cyclic carbonates from the reaction between an epoxide and $CO_2$ is developed. The catalyst preparation consists of the following stages: a) a catalytic precursor featuring either an alkylene or arylene group is obtained, which reacts with a silane compound in the presence of silica gel and xylene, b) the previously obtained product reacts with a tertiary phosphine.

In the application of the European patent EP 3023419A1 a continuous method for the production of cyclic carbonate is described. In order to accomplish this goal, a cylindrical reactor working as a packed-bed reactor was designed, which is fed with $CO_2$ and epoxide. The produced glycol is removed continuously. The employed catalyst features an active phase of either chloride or bromide salts of tetra alkyl phosphonium supported on inorganic oxides such as $SiO_2$, $Al_2O_3$, $TiO_2$, MgO, $ZrO_2$, $B_2O_3$, CaO, ZnO, BaO, and $Fe_2O_3$.

In the application of the European patent EP 3098219A1 a method for synthesizing cyclic carbonates from epoxy compounds and $CO_2$ in the presence of catalysts that feature alkaline metal halides supported on silica, for example $NaI-SiO_2$ and $LiBr-SiO_2$, is described.

The European patent 3023418 B1 presents a methodology for the continuous production of cyclic carbonates through the reaction between an epoxide and carbon dioxide. A quaternary salt either of ammonium or phosphonium is used and a halogen working as counterion on silica gel or mesoporous silica gel base and a polymer of the type polystyrene, polyethylene glycol, polyimide, polypropylene glycol and polybenzothiazole, among others. An organohalogen compound is also used to prevent the catalyst degradation and increase the reaction yield, where bromoethanol or bromopropanol are used preferably with a proportion of $2.0\text{-}3.5\times10^{-3}{:}1$ mol with respect to the epoxy compound.

In the patent application US 2004 0220433 A1 the invention of a procedure for producing propylene glycol from propylene oxide is described. The basic process consists in putting together propylene oxide and $CO_2$ in the presence of a catalyst and in the absence of water to produce propylene carbonate. The preferred employed catalyst is the tributyl (methyl)phosphonium iodide.

The patent application US 2006 0094893 A1 describes the production of cyclic carbonates, where an epoxide reacts with $CO_2$ in the presence of both a catalyst and a co-catalyst. The employed epoxides can be ethylene, propylene, butylene, chloropropylene and cyclohexene carbonates. The titanosilicate catalyst can be TS-1, TiMCM-41, Ti-beta or an amorphous titanosilicate with general formula $X\ TiO_2.(1-x)SiO_2$, where X ranges from 0.0005 to 0.04. The co-catalyst can be derived from pyridine, alkyl phosphene, aryl phosphene, alkyl ammonium salts or phosphonium salts. The employed solvent can come from a group featuring the following compounds: acetonitrile, acetone, dimethylformamide, pyridine, dioxane, water or preferably dichloromethane.

The patent application US 2007 0093672 A1 presents the design of a process for the production of organic carbonates. Such chemical reaction takes place in the presence of a single or multiple heterogeneous catalysts. Preferably Ti, Zr, Hf, Nb, Ta, Mo, V, Bi and Si supported on materials featuring hydroxyl groups such as silica.

The patent application US 2008 0214386 A1 describes the preparation and use of a solid catalyst. Such catalyst consists of an inorganic solid and a salt from an element belonging to the Group 15. It is specifically a substance that can have cations such as: phosphonium, antimony or arsenic; within the anions, the following can be mentioned: sulfates, cyanides or isothiocyanides, isocyanates, carbonates, hydrogencarbonates or halides. In general, oxides containing silicon are used as supports.

The patent application US 2016 0060242 A1 describes a method for the production of heterogeneous catalysts used in the synthesis of cyclic carbonates, which consists of 2 stages: a) a catalyst precursor is obtained, which reacts with a silane compound that has either a haloalkyl or a haloaryl group and a silicon gel; b) the previously obtained product reacts with a tertiary phosphine using a molar ratio halogen/phosphorus from 0.8 to 1.6 to finally produce the catalyst with a quaternary phosphonium group and a halide anion as counterion.

The patent application US 2017 00888535 A1 describes methods and catalysts for producing cyclic carbonates. The components of the reaction system are a catalyst that can be prepared from a polymer with ammonium quaternary salt, a metal halide supported on silica gel. Polydimethyl diallyl ammonium bromide (—$ZnBr_2$—$SiO_2$) was synthesized specifically.

In the U.S. Pat. No. 5,091,543 the procedure to carry out the preparation of cyclic carbonates using alkyl ammonium and tertiary amine catalysts is mentioned. The process consists of the reaction between the 1,2 or 1,3-diol with acyclic diester of carbonic acid in the presence of a catalyst that can be alkyl ammonium salts, tertiary amines, ionic exchange resin with alkyl ammonium or quaternary amine groups.

The patent U.S. Ser. No. 00/900,6425 B2 describes the synthesis of cyclic carbonates using dimeric aluminum catalysts, which are represented in the structure (3).

(3) Structure of the Aluminum Dimeric Catalyst

In this patent, it is stated that the presence of a co-catalyst consisting of tetraalkylammonium halide, the dimeric aluminum complexes are highly active catalysts.

The U.S. Pat. No. 9,242,955 B2 deals with the synthesis of cyclic carbonates from epoxides and $CO_2$ in the presence of aluminum dimeric salts and co-catalyzed by means of complementary salts using Cl, Br and I.

The U.S. Pat. No. 9,546,147 B2 describes the synthesis of either linear or cyclic carbonates that can be used to prepare polyurethanes or polycarbonates free of isocyanates. The reaction for producing carbonates can be with or without the use of catalysts. Among the employed catalysts, the following are found: silica, $Bi_2O_3$, $BaCO_3$, RbCl, $Na_2CO_3$, $FeCl_3$, $CoCl_2$, $SnCl_2$, $CaCO_3$, $MnCl_2$, $TiO_2$, and $MgSO_4$. The solvents to be used can be t-butanol, acetonitrile, pyridine, dimethylcarbonate or diethyl carbonate.

The U.S. Pat. No. 9,850,223 developed a methodology for the synthesis of metal catalysts for the selective formation of cyclic carbonates. The synthesized catalysts are produced from the precursor shown in the structure (4).

(4) Catalytic Precursor

Where $R_1$ can be H, alkyl groups $C_1\text{-}C_{20}$ or halogens and $R_2$ can be H, alkyl groups $C_1\text{-}C_{20}$, alkoxides groups and halogen or nitro groups.

From this precursor, a catalyst is synthesized whose general formula is shown in structure (5).

(5) Catalyst General Formula

SUMMARY OF THE INVENTION

In the present invention the formulation of a catalyst for accelerating the synthesis reaction of an organic carbonate is achieved from the corresponding carbon oxide and dioxide. The catalyst presents potassium iodide as active phase and is prepared using phosphate salts, poly(vinyl alcohol), activated carbon and aluminum oxyhydroxide is used as support. This material is submitted to different thermal treatments and presents a behavior pattern that is suitable for batch or continuous reaction systems.

The catalysts for this reaction based on KI present fast deactivation with the concomitant performance diminution. In the formulation proposed in this invention, poly (vinyl alcohol) along with phosphorus salts increase the useful life of these materials.

BRIEF DESCRIPTION OF THE FIGURES

The production of propylene carbonate follows a trend with a diminution of its concentration between the reaction times 400 and 1500 min. From this point, it presents a more or less stable performance up to 2400 min of evaluation. It is important to achieve homogeneous behavior and diminish the presence of subproducts and to this end, the following adjustments were performed: reduction of the concentration of the catalyst active phase and improvement of the heat transfer during the reaction in order to avoid the temperature increase in the packed bed. For this experimental run, it reached 200° C. above the desired reactor temperature.

Another possibility is to employ a continuous flow isothermal reactor like the one shown in FIG. 4.

FIG. 4 illustrates a reactor of the type Robinson-Mahoney. This reactor shows the particular feature of having an annular basket (A) for packing the catalytic bed and in the center there is a mechanical stirrer (B) and a cooling jacket (C) that ensures the elimination of hot spots on the catalyst surface.

Experimental runs were also performed with base materials (without active phase) and after 16 h of reaction, the yield was practically negligible (1.5%); this result is not shown in the plot.

DETAILED DESCRIPTION OF THE INVENTION

Figure 1:
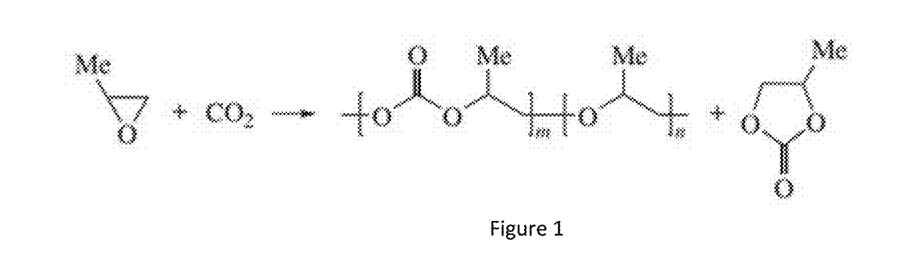
FIG. 1 shows the general reaction scheme for the cycloaddition of $CO_2$ to epoxides and the formation of cyclic carbonates, where the methyl substituent can be replaced by diverse functional groups. In the particular case of the formation of propylene carbonate, such substituent is H.
Figure 2:
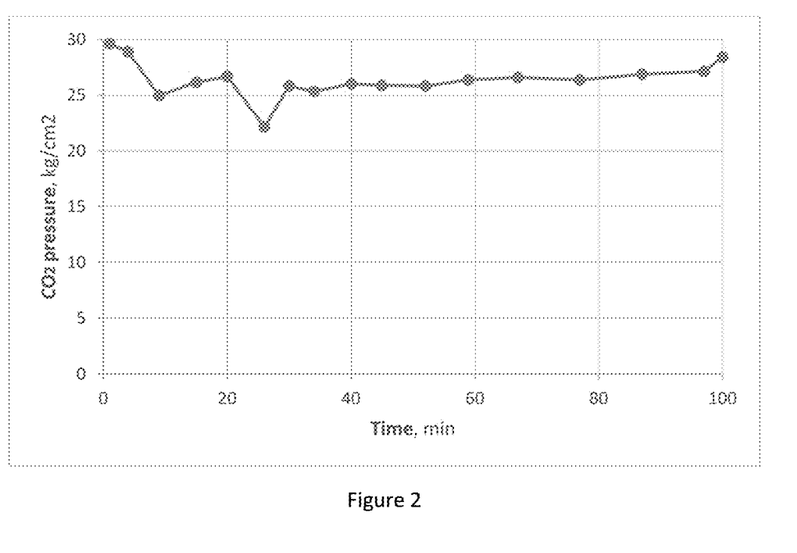
FIG. 2 displays the behavior pattern of the $CO_2$ pressure as a function of the reaction time for the cycloaddition of $CO_2$ in a batch reactor. From continuous monitoring of the pressure, it is adjusted manually to keep a nominal value of 29.5 kg/cm$^2$ of $CO_2$. Then, despite the $CO_2$ amount diminishes during the reaction, the adjustment to a constant pressure value ensures the driving force to carry out the reaction to be practically constant.
Figure 3:
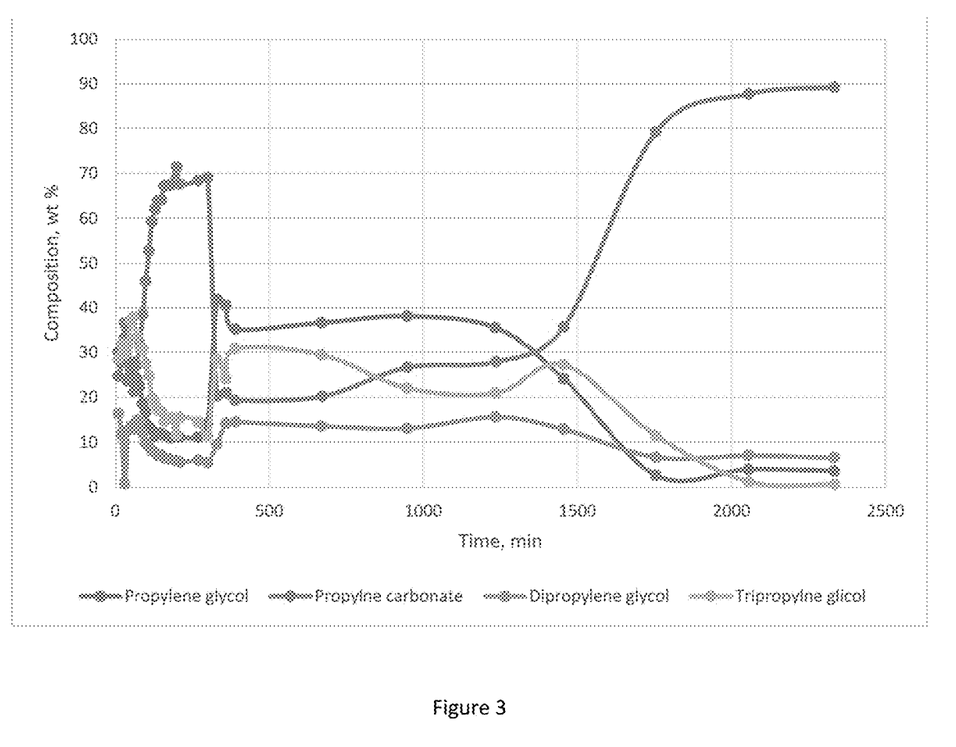
FIG. 3 shows the distribution of compound families that are obtained from the experimental evaluation of the cycloaddition reaction in a packed bed tubular reactor. The grouping of glycol compounds was carried out, giving as a result, a set for propylene glycol, di-propylene glycol and tri-propylene glycol (here even compounds known as tetraglymes were inserted). In addition, the performance of the interest product is presented: propylene carbonate.
Figure 4:
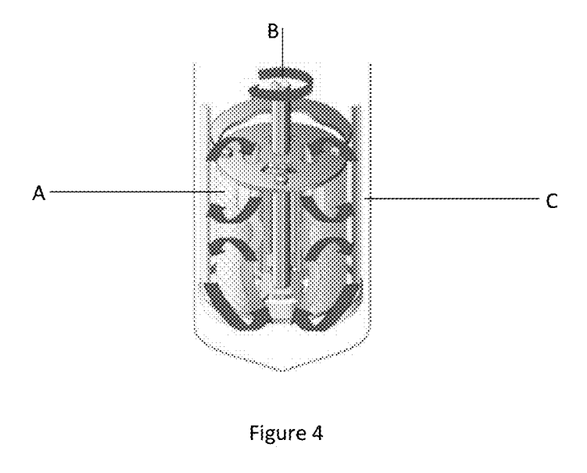
Figure 5:
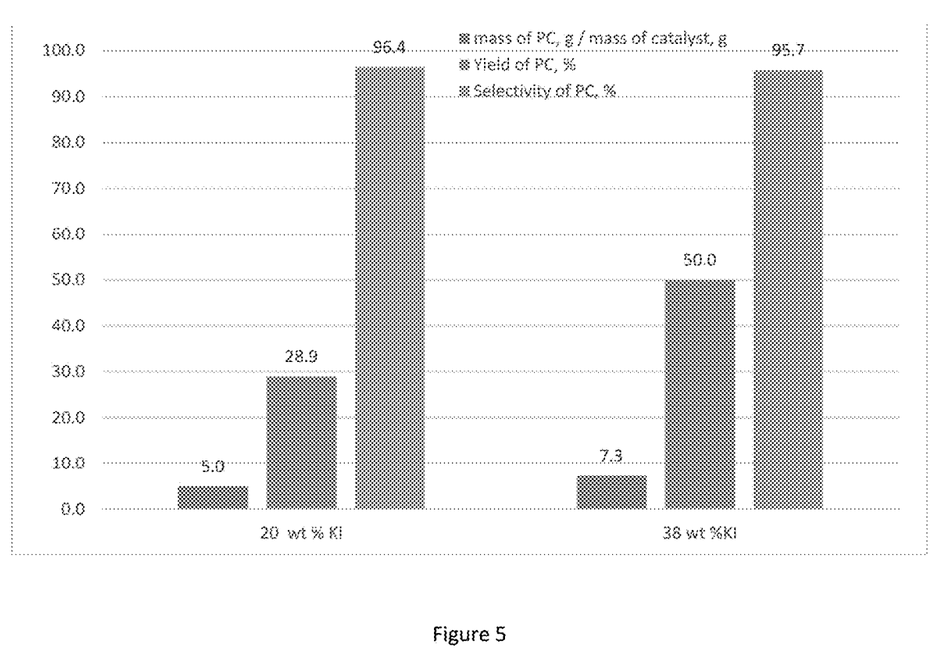
FIG. 5 displays the results of diverse experimental runs using the previously described configuration. The results after 16 h of reaction and using two catalysts with different concentrations of active phase, 20 and 38 wt. % of KI, are shown.
Figure 6:
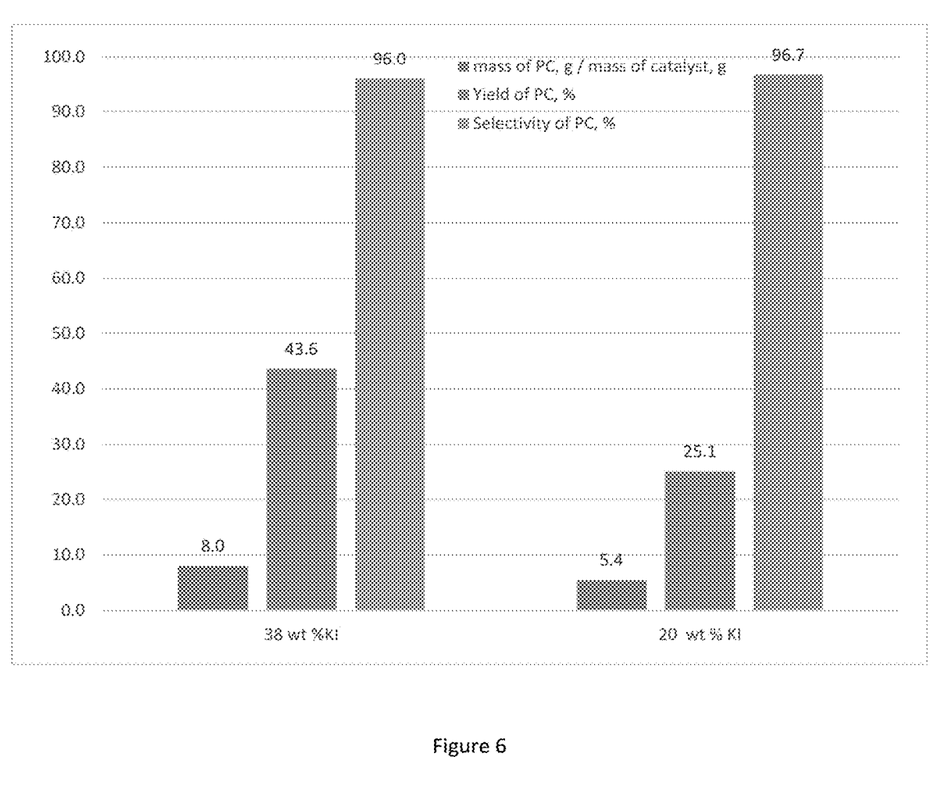
FIG. 6 shows the results of different experimental runs using the configuration of the Robinson-Mahoney reactor. The results after 20 h of reaction and using two catalysts with different concentrations of active phase, 20 and 38 wt. % of KI, are shown.

This invention deals with the synthesis of propylene cyclic carbonate from $CO_2$ and propylene oxide using catalysts whose active phase is KI supported on aluminum oxyhydroxide (Catapal B®). The catalytic formulation consists of different materials like: $NaH_2PO_4$, poly(vinyl alcohol), activated carbon (AC), nitric acid, acetic acid, and phosphoric acid. The physical and chemical conditioning of the catalytic materials was also necessary; to this end, experimental methodologies such as spheronization and thermal treatments were implemented prior the evaluation process.

In one embodiment, the invention is directed to a catalytic formulation for a cycloaddition reaction between carbon dioxide and propylene oxide for producing propylene cyclic carbonate. The catalytic formulation includes a) a support material made of an aluminum oxyhydroxide or aluminum oxide within a weight ratio between 30 and 90%; b) a carbonaceous material in a weight ratio between 1 and 60%; c) a polymeric material soluble in water or in slightly acid solutions with the presence of oxydrile groups, within a weight ratio between 1 and 45%; d) a salt promoting the presence of phosphate ions within a weight ratio between 1 and 30%; e) an aqueous acid agglutination agent at a weight ratio between 1 and 15% and f) an alkaline metal halogen within a weight ratio between 1 and 80%.

In one embodiment, the polymeric material is selected from the group consisting of poly(vinyl alcohol), chitosan, polyacrylamide, polyacrylates, and combinations thereof.

In one embodiment, the phosphate salt is selected from the group consisting of dihydrogen phosphate, monoacid phosphate, sodium phosphate, potassium phosphate, and combinations thereof.

In one embodiment, the acid agglutination agent is selected from the group consisting of aqueous solutions of formic acid, acetic acid a nitric acid, and mixtures thereof.

In one embodiment, the alkaline metal halogen comprises potassium iodide.

What follows is the detailed description of the general synthesis procedure of the catalysts. Each batch of catalytic material was synthesized to obtain, approximately, 200 g through a mixing procedure consisting of the following stages:

1) Each component is weighed according to the desired composition in each batch.
2) In an extended recipient, the main ingredients KI, Ca and Catapal B® are mixed using a nitric acid solution at 5 vol. %.
3) The mixture is homogenized. It is convenient to use the minimal amount of acid in order to get the convenient consistency for the extrusion-spheronization stage. The extrusion-spheronization stage presents diverse parameters, however, in this experimentation most of them were kept constant. Only the spinning rate of the base that shapes the spheres was varied as a function of the consistency (viscosity) of the cylindrical extrudate.
4) The calcination of the materials was carried out according to the following thermal program:
    4.1. The material is submitted to heating from ambient temperature up to 130° C. with a heating rate of 5° C./min, keeping it for 2 h.
    4.2. Afterward, it is increased from 130° C. to 450° C. at the same rate for 3 h.
    4.3. The cooling process starts from 450° C. to 130° C., and it is kept at this point for 2 h and finally from 130° C. to ambient temperature.

Example 1

Synthesis of the Potassium-Iodide-Based Catalyst

The first stage in the preparation of this catalyst consists in the dissolution of 15 g of poly(vinyl alcohol) in 300 mL of water at 90° C. with constant stirring. When it gets cold, a solution consisting of 92 g of KI and 60 mL of water is added and stirred until complete homogenization.

Afterward, such solution is evaporated in a stove at 50-60° C. The obtained solid is ground and sieved.

The other employed components are: 10 g of $NaH_2PO_4$, 12 g of activated carbon, 114 g of Catapal B® and $HNO_3$ at 5% v/v was used as wetting agent.

The integration method of the materials consists in mixing, gradually, the different solids by adding the necessary amount of nitric acid until forming a homogeneous paste. The percent composition of the solid catalyst on wet and dry basis (at its final stage) is shown in Table 1.

TABLE 1

Catalyst composition on wet (recently prepared) and dry (after thermal treatments) bases.

| Component | Composition on wet basis, wt. % | Composition on dry basis, wt. % |
|---|---|---|
| PVA | 6 | 0 |
| CA | 5 | 5.2 |
| $NaH_2PO_4$ | 4 | 4.8 |
| KI | 38 | 40 |
| Catapal | 47 | 50 |

In order to shape the catalyst as a sphere, an extrusion/spheronization process was implemented. Once the spheres were obtained, they were dried under ambient conditions for 2 h and finally they were calcined with the characteristics described in Table 2.

TABLE 2

| Calcination stages | | |
|---|---|---|
| Intervals | Temperature | Time (h) |
| $T_{AMBIENT}$-130° C. | 130° C. | 2 |
| 130° C.-450° C. | 450° C. | 3 |
| 450° C.-130° C. | 130° C. | 2 |
| 130° C.-$T_{AMBIENT}$ | — | — |

The catalytic material obtained with this procedure was ready to be evaluated in the $CO_2$ cycloaddition reaction with propylene oxide. The reaction conditions were: temperature=160° C., pressure=29.5 kg/cm² of $CO_2$, 20 g of propylene oxide, reaction time=100 min, stirring=100 rpm, catalyst mass=1 g in a batch reactor. The following values regarding propylene cyclic carbonate were obtained: yield=93.3% and selectivity=98.75%.

Example 2

The catalytic material used in this example features the same components and follows the same methodology described in Example 1, except for the absence of $NaH_2PO_4$. The reaction was performed under the same conditions of Example 1 and the obtained results were: yield=89.3% and selectivity=98.96%.

Example 3

In this example a catalyst similar to the one in Example 1 was synthesized, but without poly(vinyl alcohol). The reaction results using this catalytic material were: yield=88.61% and selectivity=96.83%.

Example 4

In this case, the catalytic material was prepared with a calcination methodology similar to the one shown in Table 2, with the difference that the maximal reached temperature was 550° C. The reaction results were: yield=69.3% and selectivity=86.60%.

Example 5

In this example, changes were carried out regarding the phosphorus compound: one concerning the phosphate incorporation methodology and other with respect to its weight proportion in the catalyst. The catalytic spheres were obtained similarly to the procedure described in Example 1. At the initial preparation stage of the catalyst, phosphate was not added, which was included afterward by means of an incipient wetness process (when the spheres were formed). The employed amount was of 0.2 g in 10 mL of water. Finally, the obtained spheres were thermally treated at 210° C. for 4 h.

The synthesis reaction for producing propylene carbonate using these materials gave a yield of 53.9% and selectivity of 98.15%.

Example 6

This example features a modification of Example 5, which consisted of incorporating sodium dihydrogen phosphate from a higher concentration solution. The synthesis of the catalytic materials was carried out with the same methodology described in Example 5, where the modification consisted in impregnating the phosphate salt by dissolving 2 g in 10 mL of water in order to increase the salt concentration and its proportion on the surface of the spherical catalyst. The results of the cycloaddition reaction employing these catalytic materials were: yield: 56.8% and selectivity: 98.74%.

Example 7

This example describes the composition of a catalyst that is similar to the one in Example 1, but without using poly(vinyl alcohol). The rest of the components were added like in Example 1 and the preparation procedures are the same as those described in Example 1. The cyclic carbonate reaction had a yield of 92.4% and a selectivity of 99.11%.

Example 8

This example shows the preparation and evaluation performed with a catalyst having higher concentration of active phase, potassium iodide, and its percent composition was the following: 50% of KI, 6% of AC, 34% of Catapal B® and 10% of $NaH_2PO_4$, and a $HNO_3$ solution (100 mL) at 5% was used as peptizing agent. The preparation, formation and calcination stages were the same as those described in Example 1. The results of the propylene cyclic carbonate reaction were: yield=96.6% and selectivity=98.24%.

Example 9

This example presents the evaluation of a catalyst containing lower concentration of active phase, potassium iodide, and its percent composition was the following: 10% of KI, 6% of AC, 74% of Catapal B®, 10% of $NaH_2PO_4$ and a $HNO_3$ solution (50 mL) at 5% was used as peptizing agent. The preparation, formation and calcination stages are the same as those described in Example 1. The results of the propylene cyclic carbonate reaction were the following: yield=68.36 and selectivity=99.01%.

Example 10

This example features the evaluation of a catalyst having lower concentration of the active phase, potassium iodide, and its percent composition was the following: 10% of KI, 6% of AC, 74% of Catapal B®, 10% of $NaH_2PO_4$ and a $HNO_3$ solution (100 mL) at 5% was used as peptizing agent. In this case, concentrated $H_3PO_4$ (3 wt. %) was added by the incipient wetness method. The preparation, formation and calcination stages are the same as those stated in Example 1. The results of the propylene cyclic carbonate reaction were the following: yield=70.31 and selectivity=88.45%.

The invention claimed is:

1. A catalytic formulation comprising:
    a) a support material made of an aluminum oxyhydroxide or aluminum oxide within a weight ratio between 30 and 90%;
    b) a carbonaceous material in a weight ratio between 1 and 60%;
    c) a polymeric material soluble in water or in slightly acid solutions with the presence of oxydrile groups, within a weight ratio between 1 and 45%;
    d) a salt promoting the presence of phosphate ions within a weight ratio between 1 and 30%;
    e) an aqueous acid agglutination agent at a weight ratio between 1 and 15%, and wherein the aqueous the acid agglutination agent is selected from the group consisting of aqueous solutions of formic acid, acetic acid, nitric acid, and mixtures thereof;
    f) an alkaline metal halogen within a weight ratio between 1 and 80%, and wherein the alkaline metal halogen comprises potassium iodide;
    g) the catalyst promoting a cycloaddition reaction between carbon dioxide and propylene oxide for producing propylene cyclic carbonate; and
    h) the catalyst having been subjected to a ramped calcination heating procedure starting at room temperature to a final temperature of 450° C. followed by cooling to room temperature.

2. The catalytic formulation according to claim 1, where the polymeric material is selected from the group consisting of poly(vinyl alcohol), chitosan, polyacrylamide, polyacrylates, and combinations thereof.

3. The catalytic formulation according to claim 1, where the phosphate salt is selected from the group consisting of dihydrogen phosphate, monoacid phosphate, sodium phosphate, potassium phosphate, and combinations thereof.

* * * * *